United States Patent
Moalem

(10) Patent No.: US 11,806,210 B2
(45) Date of Patent: Nov. 7, 2023

(54) METHOD FOR SUB-GINGIVAL INTRAORAL SCANNING

(71) Applicant: Align Technology, Inc., San Jose, CA (US)

(72) Inventor: Yosi Moalem, Nes-Ziona (IL)

(73) Assignee: Align Technology, Inc., San Jose, CA (US)

(\*) Notice: Subject to any disclaimer, the term of this patent is extended or adjusted under 35 U.S.C. 154(b) by 115 days.

(21) Appl. No.: 17/498,673

(22) Filed: Oct. 11, 2021

(65) Prior Publication Data

US 2022/0110724 A1   Apr. 14, 2022

Related U.S. Application Data

(60) Provisional application No. 63/090,601, filed on Oct. 12, 2020.

(51) Int. Cl.
| | |
|---|---|
| A61C 9/00 | (2006.01) |
| A61B 1/24 | (2006.01) |
| A61B 1/00 | (2006.01) |
| G06T 19/20 | (2011.01) |
| A61C 13/00 | (2006.01) |

(52) U.S. Cl.
CPC ........ *A61C 9/0053* (2013.01); *A61B 1/00045* (2013.01); *A61B 1/00172* (2013.01); *A61B 1/24* (2013.01); *A61C 13/0003* (2013.01); *G06T 19/20* (2013.01); *G06T 2210/41* (2013.01); *G06T 2210/62* (2013.01); *G06T 2219/2021* (2013.01)

(58) Field of Classification Search
None
See application file for complete search history.

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |
| 6,334,853 B1 | 1/2002 | Kopelman et al. |
| 6,463,344 B1 | 10/2002 | Pavlovskaia et al. |
| 6,542,249 B1 | 4/2003 | Kofman et al. |

(Continued)

OTHER PUBLICATIONS

Rajambigai et al. "Quick, painless, and atraumatic gingival retraction: An overview of advanced materials", J Pharm Bioallied Sci. Oct. 2016; 8(Suppl 1): S5-S7 (Year: 2016).*

*Primary Examiner* — Yingchun He
(74) *Attorney, Agent, or Firm* — Lowenstein Sandler LLP

(57) ABSTRACT

Methods and systems are described that receive intraoral scan data in response to an optical scan of a surface of the tooth and a material disposed between the tooth and a gingiva surrounding the tooth, the material separating the surrounding gingiva from the tooth and covering a sub-gingival surface of the tooth. The received intraoral scan data is processed to differentiate the first optical scan data associated with the sub-gingival surface of the tooth and the second optical scan data associated with the material covering the sub-gingival surface of the tooth. The three-dimensional model of the tooth is generated based on the first optical scan data that is associated with the sub-gingival surface of the tooth and the third optical scan data associated with the tooth surface that is not covered by the material such that the three-dimensional model of the tooth includes the sub-gingival surface of the tooth.

20 Claims, 9 Drawing Sheets

(56) References Cited

U.S. PATENT DOCUMENTS

| | | |
|---|---|---|
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 11,096,765 B2 | 8/2021 | Atiya et al. |
| 11,238,586 B2 | 2/2022 | Minchenkov et al. |
| 2015/0348320 A1* | 12/2015 | Pesach .............. A61C 13/0004 382/128 |
| 2018/0071061 A1* | 3/2018 | Lipovetsky ........ A61B 1/00194 |
| 2019/0029784 A1 | 1/2019 | Moalem et al. |
| 2019/0388193 A1 | 12/2019 | Saphier et al. |
| 2020/0281700 A1 | 9/2020 | Kopelman et al. |
| 2020/0281702 A1 | 9/2020 | Kopelman et al. |
| 2020/0315434 A1 | 10/2020 | Kopelman et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |

* cited by examiner

METHOD FOR SUB-GINGIVAL INTRAORAL SCANNING

RELATED APPLICATION

This application claims the benefit of provisional application No. 63/090,601, filed Oct. 12, 2020, the entire content of which are hereby incorporated by reference herein.

TECHNICAL FIELD

Embodiments of the present disclosure relate to the field of dentistry and, in particular, to the use of processing techniques for generating digital models that include a sub-gingival surface of a tooth.

BACKGROUND

For restorative dental work such as crowns and bridges, one or more intraoral scans may be generated of a preparation tooth and/or surrounding teeth on a patient's dental arch using an intraoral scanner. In cases of sub-gingival preparations, the gingiva covers at least portions of the margin line (also referred to herein as a finish line or chamfer line) and is retracted in order to fully expose the margin line. Thus, intraoral scans are generally created after a doctor packs a dental retraction cord (also referred to as packing cord or retraction cord) under the gums around the preparation tooth and then withdraws the retraction cord, briefly exposing a sub-gingival margin line. The process of packing the retraction cord between the preparation and the gums is lengthy, and can take about 10 minutes per preparation to complete. Additionally, this process is painful to the patient and can damage the gum. The intraoral scans taken after the retraction cord has been packed around the preparation tooth and then withdrawn must be taken within a narrow time window during which the gingiva collapses back over the margin line. If insufficient intraoral scans are generated before the gingiva collapses, then the process needs to be repeated. Once sufficient intraoral scans are generated, these are then used to generate a virtual three-dimensional (3D) model of a dental site including the preparation tooth and the surrounding teeth and gingiva. For example, a virtual 3D model of a patient's dental arch may be generated. The virtual 3D model may then be sent to a lab.

The lab may then perform a process called modeling in which it manually manipulates the virtual 3D model or a physical 3D model generated from the virtual 3D model to achieve a 3D model that is usable to create a crown, bridge, or other dental prosthetic. This may include manually marking a margin line in the virtual 3D model or the physical 3D model, for example. This may further include resculpting the virtual 3D model or physical 3D model, such as to correct the margin line if it is unclear or covered by gingiva in areas. Such work of modifying the virtual 3D model and/or the physical 3D model by the lab often results in an educated guess at what the actual geometry of the patient's preparation tooth is, including a guess at the margin line, a guess at the tooth's shape, and so on. A dental prosthetic may then be manufactured using the modified virtual 3D model or physical 3D model. If the guess at the true geometry of the patient's preparation tooth was incorrect, then this process is repeated, resulting in additional work on the part of the dentist and/or lab. Additionally, the process of manually modifying the virtual 3D model or physical 3D model is a time intensive task that is performed by experienced lab technicians, which increases the overall cost of the dental prosthetic and increases the amount of time that it takes to manufacture the dental prosthetic.

SUMMARY

In a first aspect of the disclosure, a method includes receiving intraoral scan data comprising first optical scan data, second optical scan data and third optical scan data in response to an optical scan of a surface of the tooth and a material disposed between the tooth and a gingiva surrounding the tooth, the material separating the surrounding gingiva from the tooth and covering a sub-gingival surface of the tooth. The method includes processing the received intraoral scan data to differentiate the first optical scan data associated with the sub-gingival surface of the tooth and the second optical scan data associated with the material covering the sub-gingival surface of the tooth. The method includes generating the three-dimensional model of the tooth based on the first optical scan data that is associated with the sub-gingival surface of the tooth and the third optical scan data associated with the tooth surface that is not covered by the material such that the three-dimensional model of the tooth includes the sub-gingival surface of the tooth.

A second aspect of the disclosure may further extend the first aspect of the disclosure. In the second aspect of the disclosure, the material is at least partially optically transparent to the optical scan.

A third aspect of the disclosure may further extend the first or second aspects of the disclosure. In the third aspect of the disclosure, the method further includes providing the generated three-dimensional model of the tooth for presentation at a display.

A fourth aspect of the disclosure may further extend the first through third aspects of the disclosure. In the fourth aspect of the disclosure, the method further includes producing a dental restoration based on the generated three-dimensional model of the tooth.

A fifth, sixth and seventh aspect of the disclosure may further extend the first aspects of the disclosure. In the fifth aspect of the disclosure, processing the received intraoral scan data to differentiate first optical scan data and second optical scan data comprises determining coordinate offset data indicative of locations on the sub-gingival surface of the tooth on which refracted optical signals that travelled through the material were incident. In the sixth aspect of the disclosure, determining the coordinate offset data includes determining angles of refraction of the refracted optical signals to determine the locations of the sub-gingival surface of the tooth on which the refracted optical signals were incident; and adjusting coordinates of the sub-gingival surface of the tooth of the first optical scan data using the coordinate offset data to account for the angles of refraction of the refracted optical signals. In the seventh aspect of the disclosure, determining the coordinate offset data comprises: determining a three-dimensional model of a surface of the material that is disposed between the tooth and the gingiva surrounding the tooth based on the second optical scan data associated with the material covering the sub-gingival surface of the tooth; and determining angles of incidence of incident optical signals that are incident on the surface of the material.

In an eight aspect of the disclosure, a computer readable medium stores instructions that, when executed by a processing device, cause the processing device to execute the methods of any of the $1^{st}$ through the $7^{th}$ aspects of the disclosure.

In a ninth aspect of the disclosure, a computing device comprises a memory and a processing device operably coupled to the memory, wherein the processing device is to execute instructions from the memory which cause the processing device to perform the methods of any of the $1^{st}$ through the $7^{th}$ aspects of the disclosure.

In a tenth aspect of the disclosure, a system includes an optical probe of an intraoral scanner and a an optical imaging device operably coupled to the optical probe, wherein the intraoral scanner is to generate scan data and the computing device is to execute the methods of any of the $1^{st}$ through the $7^{th}$ aspects of the disclosure.

BRIEF DESCRIPTION OF THE DRAWINGS

Embodiments of the present disclosure are illustrated by way of example, and not by way of limitation, in the figures of the accompanying drawings.

DETAILED DESCRIPTION

Figure 1A:
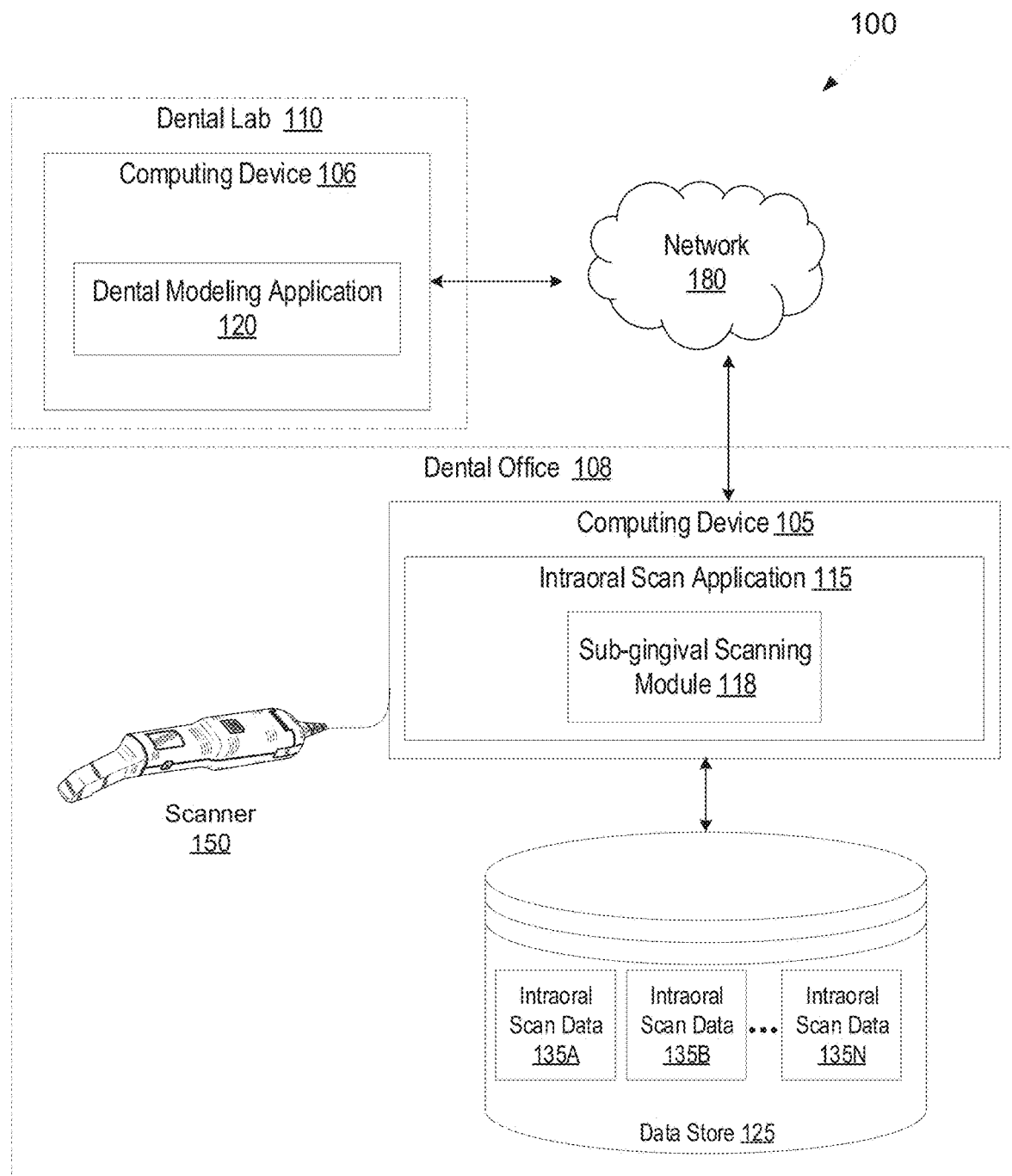
FIG. 1A illustrates one embodiment of a system for performing intraoral scanning and/or generating a virtual three-dimensional model of an intraoral site.

Described herein are methods and systems for accurately determining the shape, position and orientation of sub-gingival preparations of a tooth, such as a sub-gingival margin line of a preparation tooth. For many prosthodontic procedures (e.g., to create a crown, bridge, veneer, etc.), an existing tooth of a patient is ground down to a stump. The ground tooth is referred to herein as a preparation tooth, or simply a preparation. The preparation tooth has a margin line (also referred to as a chamfer line), which is a border between a natural (unground) portion of the preparation tooth and the prepared (ground) portion of the preparation tooth. The preparation tooth is typically created so that a crown or other prosthesis can be mounted or seated on the preparation tooth. In many instances, the margin line of the preparation tooth is sub-gingival (below the gum line). While the term preparation typically refers to the stump of a preparation tooth, including the margin line and shoulder that remains of the tooth, the term preparation herein also includes artificial stumps, pivots, cores and posts, or other devices that may be implanted in the intraoral cavity so as to receive a crown or other prosthesis. Embodiments described herein with reference to a preparation tooth also apply to other types of preparations, such as the aforementioned artificial stumps, pivots, and so on.

After the preparation tooth is created, a practitioner performs operations to ready that preparation tooth for scanning. Readying the preparation tooth for scanning may include wiping blood, saliva, etc. off of the preparation tooth and/or separating a patient's gum from the preparation tooth to expose the margin line. In some instances, a practitioner will insert a material (e.g., a retraction material such as a retraction cord) around the preparation tooth between the preparation tooth and the patient's gum. The practitioner will then remove the cord before generating a set of intraoral scans of the preparation tooth. After removal of the cord, the soft tissue of the gum will then revert back to its natural position, and in many cases collapses back over the margin line, after a brief time period. Accordingly, the practitioner uses an intraoral scanner to scan the readied preparation tooth and generate a set of intraoral images of the preparation tooth before the soft tissue reverts back to its natural position. The intraoral site at which a prosthesis is to be implanted generally should be measured accurately and studied carefully, so that the prosthesis such as a crown, denture or bridge, for example, can be properly designed and dimensioned to fit in place. A good fit enables mechanical stresses to be properly transmitted between the prosthesis and the jaw, and can prevent infection of the gums and tooth decay via the interface between the prosthesis and the intraoral site, for example. After the intraoral site has been scanned, a virtual 3D model (also referred to herein simply as a 3D model) of the dental site may be generated, and that 3D model may be used to manufacture a dental prosthetic. However, if the area of a preparation tooth containing the margin line lacks definition, it may not be possible to properly determine the margin line, and thus the margin of a restoration may not be properly designed.

In some systems, the retraction cord is placed well below a patient's margin line (in the direction of the root of the tooth) so that the practitioner has enough clearance below the margin line to generate accurate intraoral scans and to give the practitioner more time to complete the intraoral scanning before the gum reverts back to its natural position. Separating a patient's gum from the preparation tooth to expose the margin line can damage a patient's gums and the damage can be exacerbated the more the surface of the preparation tooth is exposed below the margin line. Moreover, the gum often reverts back to its natural position before a practitioner can complete a scanning, resulting in inaccurate or incomplete intraoral scans. Often and because the gum has reverted back to its natural positon before a scanning is complete, the practitioner repeats the above actions to prepare the preparation tooth for a subsequent intraoral scanning.

Aspects of the disclosure address the above and additional challenges by using a material that is disposed between the tooth (e.g. preparation tooth) and the gingiva surrounding the tooth. The material can separate the surrounding gingiva from the tooth and cover the sub-gingival surface of the tooth. The sub-gingival surface can include the margin line, and in some cases a sub-gingival surface of the preparation tooth below the margin line. The material holds the gum away from the sub-gingival surface of the preparation tooth while an intraoral scanning procedure (e.g., optical scan) is performed. The gums do not need to expose as much sub-gingival surface of the preparation tooth below the margin line as some conventional systems at least because the material holds the gum away from the sub-gingival surface of the preparation tooth for the duration of the scanning and prevents the gum from collapsing back over the sub-gingival surface to be scanned.

An intraoral scanning procedure that emits optical signals from a probe of an intraoral scanner can be performed to gather information about surfaces on which the optical signals are incident. Some of the optical signals travel in air from the probe to the surface of the material (are incident on the surface of the material) and at least parts of the optical signals are reflected off of the surface of the material back to the probe. Some of the optical signals travel in air from the probe to the surface of the material and are refracted and traverse the material and are incident upon the sub-gingival surface of the tooth, after which at least parts of the optical signals are reflected back to the probe. The optical signals that traverse the material are refracted due to the difference in refractive index between the air and the material. From the intraoral scanning, an intraoral scan (e.g., intraoral scan data) is generated that includes first optical scan data of a sub-gingival surface of the preparation tooth, second optical scan data of the material overlying the sub-gingival surface of the tooth and third optical scan data associated with the tooth surface that is not covered by the material. In some instances the first optical scan data of the sub-gingival surface of the preparation tooth may not account for the refracted optical signals. In some embodiments, the intraoral scan is processed to differentiate the first optical scan data associated with the sub-gingival surface of the tooth from the second optical scan data associated with the material covering the sub-gingival surface of the tooth. In at least some embodiments, to differentiate the first optical scan data from the second optical scan data (e.g., to compensate for refracted optical signals), the first optical scan data of a sub-gingival surface of the preparation tooth is adjusted using coordinate offset data to account for the angles of refraction of the refracted optical signals. Using the adjusted first optical scan data, the sub-gingival surface of the preparation tooth is determined and a three-dimensional model of the preparation tooth including the sub-gingival surface of the preparation tooth is generated.

Therefore, advantages of the systems and methods implemented in accordance with some embodiments of the disclosure include, but are not limited to, improving the accuracy and completeness of intraoral scans, and improving the accuracy and completeness of a 3D model that includes a sub-gingival surface of a preparation tooth, which in turn improves the design of dental prosthetics for the preparation tooth. Additionally, advantages of the systems and methods implemented in accordance with some embodiments of the disclosure include, but are not limited to, obtaining improved intraoral scans while contributing less damage to a patient's gums.

Various embodiments are described herein. It should be understood that these various embodiments may be implemented as stand-alone solutions and/or may be combined. Accordingly, references to an embodiment, or one embodiment, may refer to the same embodiment and/or to different embodiments. Additionally, some embodiments are discussed with reference to restorative dentistry, and in particular to preparation teeth and margin lines. However, it should be understood that embodiments discussed with reference to restorative dentistry (e.g., prosthodontics) may also apply to corrective dentistry (e.g., orthodontia). Additionally, embodiments discussed with reference to preparation teeth may also apply to teeth generally, and not just preparation teeth. Furthermore, embodiments discussed with reference to margin lines may also apply to other dental features, such as cracks, chips, gum lines, caries, and so on, and in particular dental features on the sub-gingival surface of a tooth.

FIG. 1A illustrates one embodiment of a system 100 for performing intraoral scanning and/or generating a virtual three-dimensional model of an intraoral site. In one embodiment, one or more components of system 100 carries out one or more operations described below with reference to FIGS. 2A through 5B.

System 100 includes a dental office 108 and a dental lab 110. The dental office 108 and the dental lab 110 each include a computing device 105, 106, where the computing devices 105, 106 may be connected to one another via a network 180. The network 180 may be a local area network (LAN), a public wide area network (WAN) (e.g., the Internet), a private WAN (e.g., an intranet), or a combination thereof.

Computing device 105 may be coupled to an intraoral scanner 150 (also referred to as a scanner) and/or a data store 125. Computing device 106 may also be connected to a data store (not shown). The data stores may be local data stores and/or remote data stores. Computing device 105 and computing device 106 may each include one or more processing devices, memory, secondary storage, one or more input devices (e.g., such as a keyboard, mouse, tablet, and so on), one or more output devices (e.g., a display, a printer, etc.), and/or other hardware components.

Intraoral scanner 150 may include a probe (e.g., a hand held probe) for optically capturing three-dimensional structures. The intraoral scanner 150 may be used to perform an intraoral scan of a patient's oral cavity. An intraoral scan application 115 running on computing device 105 may communicate with the scanner 150 to effectuate the intraoral scan. A result of the intraoral scan may be intraoral scan data 135A, 135B through 135N that may include one or more sets of intraoral scans or images. Each intraoral image may be a two-dimensional (2D) or 3D image that includes a height map of a portion of a dental site, and may include x, y and z information. In one embodiment, the intraoral scanner 150 generates numerous discrete (i.e., individual) intraoral scans or images. Sets of discrete intraoral images may be merged into a smaller set of blended intraoral images, where each blended image is a combination of multiple discrete images. The scanner 150 may transmit the intraoral scan data 135A, 135B through 135N to the computing device 105. Computing device 105 may store the intraoral scan data 135A-135N in data store 125.

According to an example, a user (e.g., a practitioner) may subject a patient to intraoral scanning. In doing so, the user may apply scanner 150 to one or more patient intraoral locations. The scanning may be divided into one or more segments. As an example, the segments may include a lower buccal region of the patient, a lower lingual region of the patient, an upper buccal region of the patient, an upper lingual region of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral image data sets, each of which may include 2D intraoral images and/or 3D intraoral images of particular teeth and/or regions of an intraoral site. In one embodiment, separate image data sets are created for the maxillary arch, for the mandibular arch, for a patient bite, and for each preparation tooth. Alternatively, a single large intraoral image data set is generated (e.g., for a mandibular and/or maxillary arch). Such images or scans may be provided from the scanner to the computing device 105 in the form of one or more points (e.g., one or more pixels and/or groups of pixels). For instance, the scanner 150 may provide such a 3D image as one or more point clouds. The intraoral images or scans may each comprise a height map that indicates a depth for each pixel.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Additionally, the manner in which the oral cavity is to be scanned may depend on a doctor's scanning preferences and/or patient conditions. For example, some doctors may perform an intraoral scan (e.g., in a standard preparation scanning mode) after using a retraction cord to expose a margin line of a preparation. Other doctors may use a partial retraction scanning technique in which only portions of the margin line are exposed and scanned at a time (e.g., performing a scan in a partial retraction scanning mode). In one or more embodiments, a doctor injects an at least partially-transparent material between the preparation and gingiva of a patient to expose some or all of the margin line for scanning.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at an intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

For many prosthodontic procedures (e.g., to create a crown, bridge, veneer, etc.), a preparation tooth is created (e.g., by grinding a portion of a tooth to a stump). The preparation tooth has a margin line that can be important to proper fit of a dental prosthesis. After the preparation tooth is created, a practitioner performs operations to ready that preparation tooth for scanning. Readying the preparation tooth for scanning may include wiping blood, saliva, etc. off of the preparation tooth and/or separating a patient's gum from the preparation tooth to expose the margin line using one or more tools. In one or more embodiments, a doctor or other dental practitioner injects an at least partially transparent material between a preparation and surrounding gingiva. The material may be partially transparent or fully transparent to one or more wavelengths of light, which may be wavelengths of light emitted by the scanner 150 during scanning (e.g., during an optical scan). Use of the at least partially transparent material to expose the margin line and/or other sub-gingival features is discussed in greater detail below.

When a scan session is complete (e.g., all images or scans for an intraoral site or dental site have been captured), intraoral scan application 115 may generate a virtual 3D model of one or more scanned dental sites. To generate the virtual 3D model, intraoral scan application 115 may register and "stitch" or merge together the intraoral images/scans generated from the intraoral scan session. In one embodiment, performing image registration includes capturing 3D data of various points of a surface in multiple images (views from a camera), and registering the images by computing transformations between the images. The 3D data may be in the form of multiple height maps, which may be projected into a 3D space of a 3D model to form a portion of the 3D model. The images/scans may be integrated into a common reference frame by applying appropriate transformations to points of each registered image and projecting each image into the 3D space.

In one embodiment, image registration is performed for adjacent or overlapping intraoral images (e.g., each successive frame of an intraoral video). In one embodiment, image registration is performed using blended images. Image registration algorithms are carried out to register two adjacent intraoral images (e.g., two adjacent blended intraoral images) and/or to register an intraoral image with a 3D model, which essentially involves determination of the transformations which align one image with the other image and/or with the 3D model. Image registration may involve identifying multiple points in each image (e.g., point clouds) of an image pair (or of an image and the 3D model), surface fitting to the points, and using local searches around points to match points of the two images (or of the image and the 3D model). For example, intraoral scan application 115 may match points of one image with the closest points interpolated on the surface of another image, and iteratively minimize the distance between matched points. Other image registration techniques may also be used.

Intraoral scan application 115 may repeat image registration for all images of a sequence of intraoral images to obtain transformations for each image, to register each image with the previous one and/or with a common reference frame (e.g., with the 3D model). Intraoral scan application 115 integrates all images into a single virtual 3D model by applying the appropriate determined transformations to each of the images. Each transformation may include rotations about one to three axes and translations within one to three planes.

Intraoral scan application 115 may generate a 3D model from intraoral images, and may display the 3D model to a user (e.g., a doctor) via a user interface. The 3D model can then be checked visually by the doctor. The doctor can virtually manipulate the 3D model via the user interface with respect to up to six degrees of freedom (i.e., translated and/or rotated with respect to one or more of three mutually orthogonal axes) using suitable user controls (hardware and/or virtual) to enable viewing of the 3D model from any desired direction. The doctor may review (e.g., visually inspect) the generated 3D model of an intraoral site and determine whether the 3D model is acceptable (e.g., whether a margin line of a preparation tooth is accurately represented in the 3D model).

Intraoral scan application 115 may include logic for automatically identifying (e.g., highlighting) a margin line in an image and/or 3D model of a preparation tooth. This may make it easier for the doctor to inspect the margin line for accuracy. Intraoral scan application 115 may additionally mark and/or highlight specific segments of the margin line that are unclear, uncertain, and/or indeterminate. Additionally, or alternatively, intraoral scan application 115 may mark and/or highlight specific areas (e.g., a surface) that is unclear, uncertain and/or indeterminate. For example, segments of the margin line that are acceptable may be shown in a first color (e.g., green), while segments of the margin line that are unacceptable may be shown in a second color (e.g., red). If portions of the margin line are determined to be unclear or covered by gingiva, a practitioner may be advised by intraoral scan application 115 to rescan those portions of the margin line.

Once the doctor (e.g., dentist) has determined that the 3D model is acceptable, the doctor may instruct computing device 105 to send the 3D model to computing device 106 of dental lab 110. Computing device 106 may include a dental modeling application 120 that may analyze the 3D model to determine if it is adequate for manufacture of a dental prosthetic. Dental modeling application 120 may include logic to identify the margin line and/or to modify the surface of one or more dental sites and/or to modify a margin line, as discussed with reference to intraoral scan application 115. If the 3D model is deemed suitable (or can be modified such that it is placed into a condition that is deemed suitable), then the dental prosthetic may be manufactured from the 3D model. If the 3D model cannot be placed into a suitable condition, then instructions may be sent back to the dental office 108 to generate one or more additional intraoral images of one or more regions of the dental site.

In some embodiments, intraoral scan application 115 includes sub-gingival scanning module 118. In some embodiments, sub-gingival scanning module 118 can perform aspects of the disclosure, including one or more operations as described herein. For example and in some embodiments, scanning of a preparation (e.g., such as a preparation tooth) is performed after injecting an at least partially transparent material between the preparation and a surrounding gingiva to expose a sub-gingival surface of the preparation. Intraoral scans received by sub-gingival scanning module 118 may include first optical scan data of a sub-gingival surface of a tooth of a patient and second optical scan data of an at least partially transparent material overlying the sub-gingival surface of the tooth. The at least partially transparent material is disposed between a gingiva of the patient and the sub-gingival surface of the tooth and separates the gingiva from the sub-gingival surface of the tooth. The sub-gingival scanning module 118 distinguishes between the surface of the at least partially transparent material and the underlying sub-gingival surface in embodiments. In one embodiment, the sub-gingival scanning module 118 determines coordinate offset data indicative of locations on the sub-gingival surface of the tooth on which refracted optical signals that travelled through the at least partially transparent material were incident. The sub-gingival scanning module 118 may determine the sub-gingival surface of the tooth based on applying the coordinate offset data to the first optical scan data. The sub-gingival scanning module 118 may generate a three-dimensional (3D) model of the tooth based at least in part on the intraoral scan. The 3D model of the tooth includes the determined sub-gingival surface of the tooth.

Figure 1B:
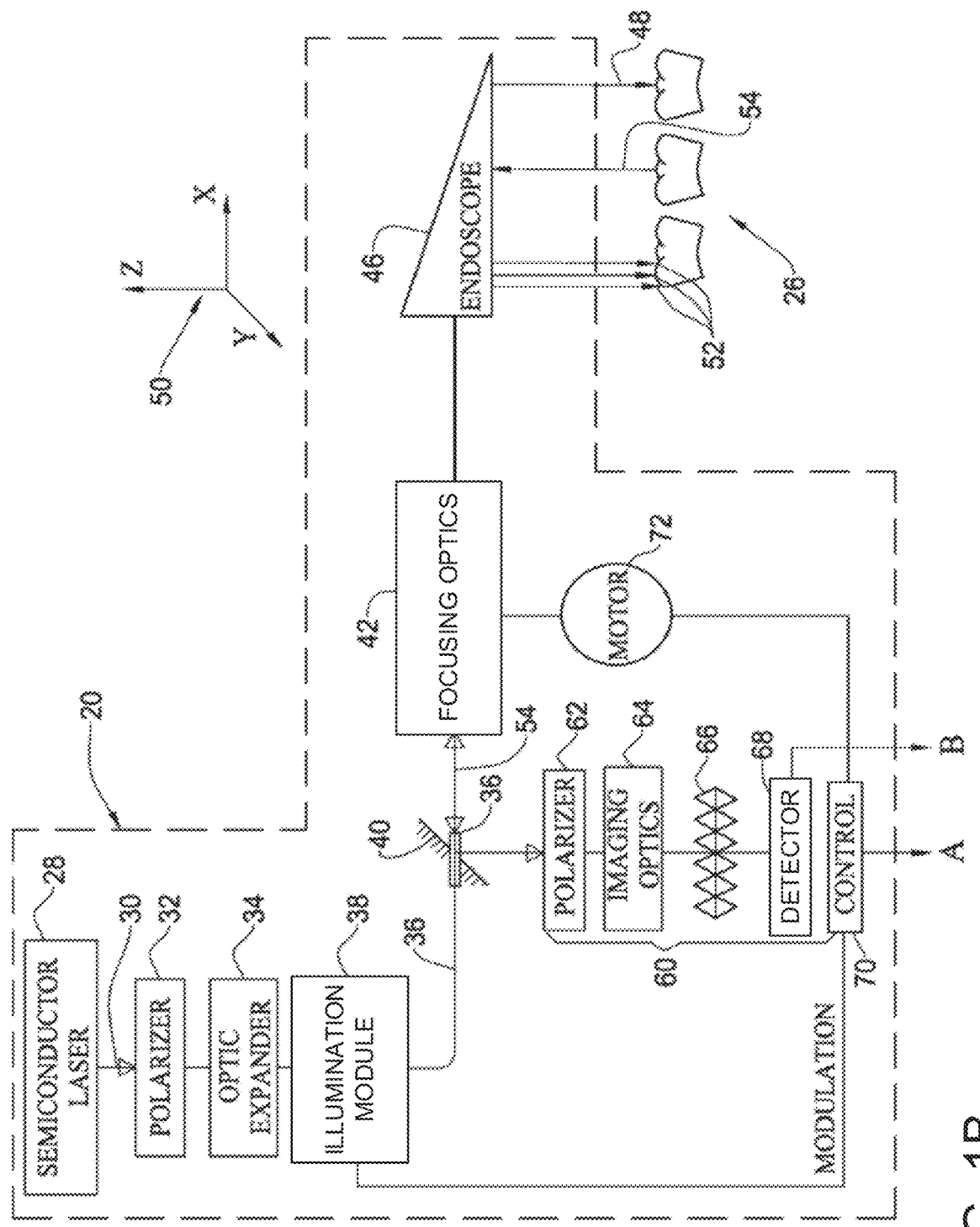
FIG. 1B illustrates a functional block diagram of an intraoral scanner according to one embodiment.
Figure 1C:
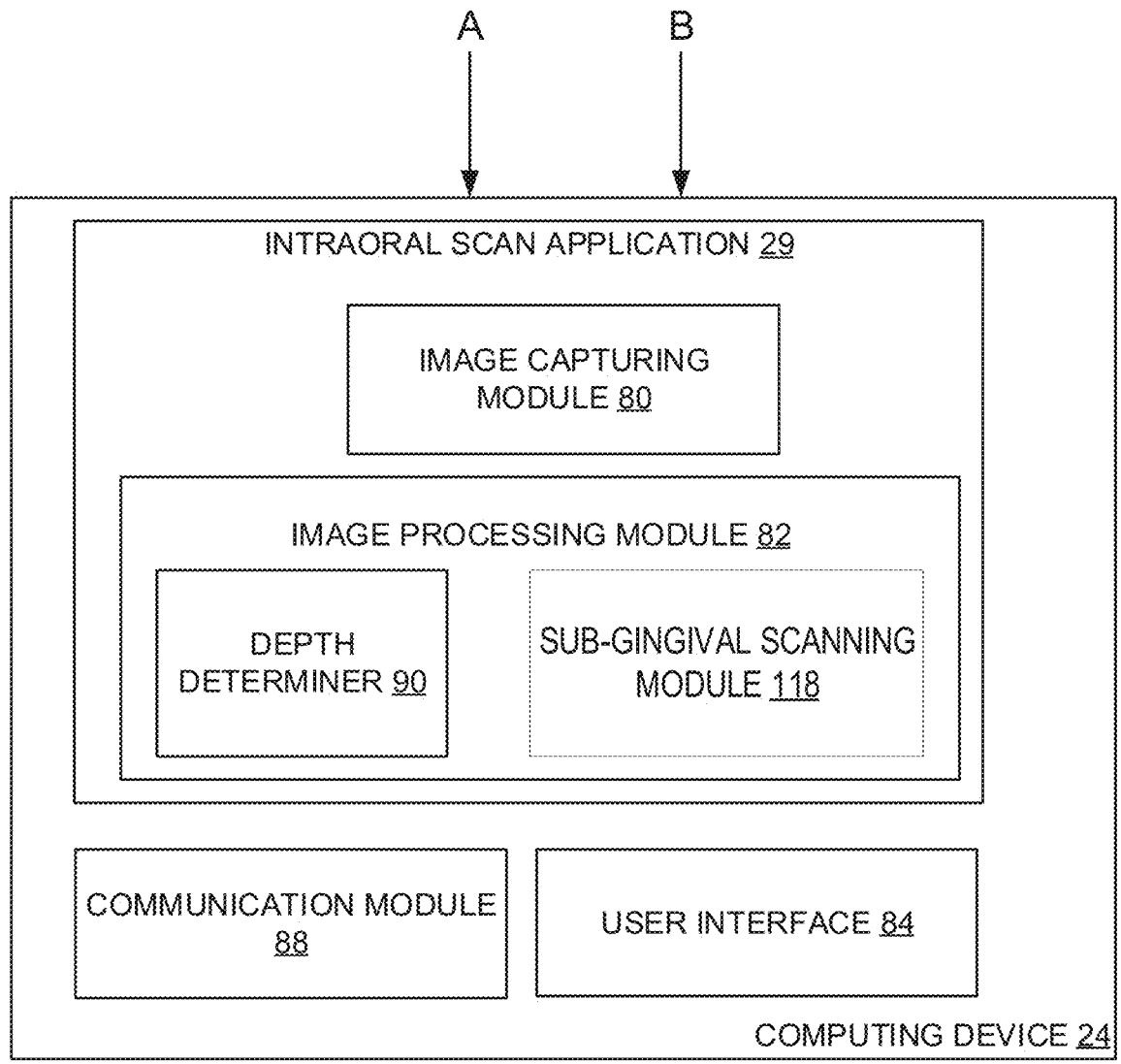
FIG. 1C illustrates a block diagram of a computing device that connects to a confocal imaging apparatus, in accordance with one embodiment.

FIG. 1B illustrates a functional block diagram of an intraoral scanner 20, which may correspond to scanner 150 of FIG. 1A in embodiments. Intraoral scanner 20 may be a confocal scanner according to one embodiment. FIG. 1C illustrates a block diagram of a computing device 24 that connects to the scanner 20. In embodiments, computing device 24 corresponds to computing device 105 of FIG. 1A. Together, the intraoral scanner 20 and computing device 24 may form a system for generating three dimensional images of scanned intraoral objects, referred to as an intraoral scanning system. The computing device 24 may be connected to the scanner 20 directly or indirectly and via a wired or wireless connection. For example, the scanner 20 may include a network interface controller (NIC) capable of communicating via Wi-Fi, via third generation (3G) or fourth generation (4G) telecommunications protocols (e.g., global system for mobile communications (GSM), long term evolution (LTE), Wi-Max, code division multiple access (CDMA), etc.), via Bluetooth, via Zigbee, or via other wireless protocols. Alternatively, or additionally, scanner 20 may include an Ethernet network interface controller (NIC), a universal serial bus (USB) port, or other wired port. The NIC or port may connect the confocal imaging apparatus to the computing device via a local area network (LAN). Alternatively, the scanner 20 may connect to a wide area network (WAN) such as the Internet, and may connect to the computing device 24 via the WAN. In an alternative embodiment, scanner 20 is connected directly to the computing device (e.g., via a direct wired or wireless connection). In one embodiment, the computing device 24 is a component of the scanner 20.

Referring now to FIG. 1B, in one embodiment scanner 20 includes a semiconductor laser unit 28 or other light source that emits light such as a focused light beam, as represented by arrow 30. The light 30 passes through a polarizer 32. Polarizer 32 polarizes the light passing through polarizer 32. Alternatively, polarizer 32 may be omitted in some embodiments. The light then enters into an optic expander 34 that improves a numerical aperture of the light beam 30. In one embodiment, the light 30 passes through an illumination module 38, which splits the light 30 into an array of incident light beams, represented here, for ease of illustration, by a single line. Alternatively, the illumination module 38 may impart some image pattern on the light. The illumination module 38 may be, for example, a grating or a micro lens array that splits the light 30 into an array of light beams.

Alternatively, the illumination model may be a checkerboard pattern or other static or time varying pattern that causes light passing therethrough to have the pattern. Modified light 36 (e.g., patterned light and/or an array of light beams) is output by the illumination module 38.

The scanner 20 may further include a unidirectional mirror or beam sputter (e.g., a polarizing beam splitter) 40 that passes the modified light 36. A unidirectional mirror 40 allows transfer of light from the semiconductor laser 28 or other light source through to downstream optics, but reflects light travelling in the opposite direction. A polarizing beam splitter allows transfer of light having a particular polarization and reflects light having a different (e.g., opposite) polarization. In one embodiment, the unidirectional mirror or beam splitter 40 has a small central aperture. The small central aperture may improve a measurement accuracy of the scanner 20. In one embodiment, as a result of a structure of the unidirectional mirror or beam sputter 40, the modified light will yield a light annulus on an illuminated area of an imaged object as long as the area is not in focus. Moreover, the annulus will become a completely illuminated spot or point once in focus. This ensures that a difference between measured intensities of out-of focus points and in-focus points will be larger.

Along an optical path of the modified light after the unidirectional mirror or beam splitter 40 are focusing optics 42 (which may or may not be confocal imaging optics), and an endoscopic probing member 46. Additionally, a quarter wave plate may be disposed along the optical path after the unidirectional mirror or beam splitter 40 to introduce a certain polarization to the modified light. In some embodiments this may ensure that reflected light will not be passed through the unidirectional mirror or beam splitter 40. Focusing optics 42 may additionally include relay optics (not shown). Focusing optics 42 may or may not maintain the same magnification of an image over a wide range of distances in the Z direction, wherein the Z direction is a direction of beam propagation (e.g., the Z direction corresponds to an imaging axis that is aligned with an optical path of the modified light 36). The relay optics enable the scanner 20 to maintain a certain numerical aperture for propagation of the modified light 36.

The endoscopic probing member 46 may include a rigid, light-transmitting medium, which may be a hollow object defining within it a light transmission path or an object made of a light transmitting material, e.g. a glass body or tube. In one embodiment, the endoscopic probing member 46 include a prism such as a folding prism. At its end, the endoscopic probing member 46 may include a mirror of the kind ensuring a total internal reflection. Thus, the mirror may direct the modified light towards a teeth segment 26 or other object. The endoscope probing member 46 thus emits modified light 48 (e.g., an array of light beams and/or patterned light), which impinge on to surfaces of the teeth section 26.

The modified light 48 are arranged in an X-Y plane, in the Cartesian frame 50, propagating along the Z axis. As the surface on which the incident light hits is an uneven surface, illuminated points 52 are displaced from one another along the Z axis, at different $(X_i, Y_i)$ locations. Thus, while a point at one location may be in focus of the confocal focusing optics 42, points at other locations may be out-of-focus. Therefore, the light intensity of returned light of the focused points will be at its peak, while the light intensity at other points will be off peak. Thus, for each illuminated point or area, multiple measurements of light intensity are made at different positions along the Z-axis. For each of such $(X_i, Y_i)$ location, the derivative of the intensity over distance (Z) may be made, with the $Z_i$ yielding maximum derivative, $Z_0$, being the in-focus distance. In one embodiment, the incident light from an array of light beams forms a light disk on the surface when out of focus and a complete light spot when in focus. Thus, the distance derivative will be larger when approaching in-focus position, increasing accuracy of the measurement.

The light scattered from each of the light points may include a beam travelling initially in the Z axis along the opposite direction of the optical path traveled by the modified light 48. Returned light 54 is received by the endoscope 46 and directed back through focusing optics 42. In one embodiment, a returned light beam (e.g., which may be from an array of returning light beams) corresponds to one of an array of incident light beams. Given the asymmetrical properties of unidirectional mirror or beam splitter 40, the returned light is reflected in the direction of detection optics 60.

The detection optics 60 may include a polarizer 62 that has a plane of preferred polarization oriented normal to the plane polarization of polarizer 32. Alternatively, polarizer 32 and polarizer 62 may be omitted in some embodiments. The returned light 54 may pass through imaging optics 64 in one embodiment. The imaging optics 64 may be one or more lenses. Alternatively, the detection optics 60 may not include imaging optics 64. In one embodiment, the returned light 54 further passes through a matrix 66, which may be an array of pinholes. Alternatively, no matrix 66 is used in some embodiments. The returned light 54 is then directed onto a detector 68.

The detector 68 is an image sensor having a matrix of sensing elements each representing a pixel of the image or scan. If matrix 66 is used, then each pixel further corresponds to one pinhole of matrix 66. In one embodiment, the detector is a charge coupled device (CCD) sensor. In one embodiment, the detector is a complementary metal-oxide semiconductor (CMOS) type image sensor. Other types of image sensors may also be used for detector 68. The detector 68 detects light intensity at each pixel.

In one embodiment, detector 68 provides data to computing device 24. Thus, each light intensity measured in each of the sensing elements of the detector 68, is then captured and analyzed, in a manner to be described below, by processor 24.

Confocal imaging apparatus 20 further includes a control module 70 connected both to semiconductor laser 28 or other light source and a motor 72, voice coil or other translation mechanism. In one embodiment, control module 70 is or includes a field programmable gate array (FPGA) configured to perform control operations. Motor 72 is linked to focusing optics 42 for changing a focusing setting of focusing optics 42. This may adjust the relative location of a focal surface of focusing optics 42 along the Z-axis (e.g., in the imaging axis). Control module 70 may induce motor 72 to axially displace (change a location of) one or more lenses of the focusing optics 42 to change the focal depth of the focal surface. In one embodiment, motor 72 or imaging apparatus 20 includes an encoder (not shown) that accurately measures a position of one or more lenses of the focusing optics 42. The encoder may include a sensor paired to a scale that encodes a linear position. The encoder may output a linear position of the one or more lenses of the confocal focusing optics 42. The encoder may be an optical encoder, a magnetic encoder, an inductive encoder, a capacitive encoder, an eddy current encoder, and so on. After receipt of feedback that the location of the one or more lenses has changed, control module 70 may induce laser 28 or other light source to generate a light pulse. Control unit 70 may additionally synchronize image-capturing module 80 from FIG. 1C to receive and/or store data representative of the light intensity from each of the sensing elements at the particular location of the one or more lenses (and thus of the focal depth of the imaginary non-flat focal surface). In subsequent sequences, the location of the one or more lenses (and thus the focal depth) will change in the same manner and the data capturing will continue over a wide focal range of focusing optics 42.

Referring now to FIG. 1C, computing device 24 includes an intraoral scan application 29 including an image capture module 80 and an image processing module 82. Image capturing module 80 may capture images responsive to receiving image capture commands from the control unit 70. The captured images may be associated with a particular focusing setting (e.g., a particular location of one or more lenses in the focusing optics as output by the encoder). In one embodiment, image processing module 82 then processes captured images or scans captured over multiple different focusing settings. Image processing module 82 includes a depth determiner 90 and a sub-gingival scanning module 118 in one embodiment. Alternatively, sub-gingival scanning module 118 may be distinct from image processing module 82 and/or may be combined with depth determiner 90.

Depth determiner 90 may determine the relative intensity in each pixel over the entire range of focal settings of focusing optics 42 from received image data. Once a certain light point associated with a particular pixel is in focus, the measured intensity will be maximal for that pixel. Thus, by determining the $Z_i$ corresponding to the maximal light intensity or by determining the maximum displacement derivative of the light intensity, for each pixel, the relative position of each point of light along the Z axis can be determined for each pixel. Thus, data representative of the three-dimensional pattern of a surface in the teeth segment 26 or other three dimensional object can be obtained.

In embodiments, an at least partially transparent material is used to expose a sub-gingival surface prior to scanning. In such an embodiment, two different intensity peaks may be associated with the same pixel, where one of the peaks represents a surface of the material and another peak represents the sub-gingival surface. In one embodiment, sub-gingival scanning module 118 is responsible for identifying and separating out data representing a sub-gingival surface and data representing a surface of a transparent or partially transparent material in such instances.

A three-dimensional representation may be constructed based on the corrected measurement data and displayed via a user interface 84. The user interface 84 may be a graphical user interface that includes controls for manipulating a display of the three-dimensional representation (e.g., viewing from different angles, zooming-in or out, etc.). In addition, data representative of the surface topology of the scanned intraoral object may be transmitted to remote devices by a communication module 88 for further processing or use (e.g., to generate a three dimensional virtual model of the scanned object).

By capturing, in this manner, an image from two or more angular locations around the structure, e.g. in the case of a teeth segment from the buccal direction, from the lingual direction and optionally from above the teeth, an accurate three-dimensional representation of the teeth segment may be reconstructed. This may allow a virtual reconstruction of the three-dimensional structure in a computerized environment or a physical reconstruction in a CAD/CAM apparatus.

Figure 2A:
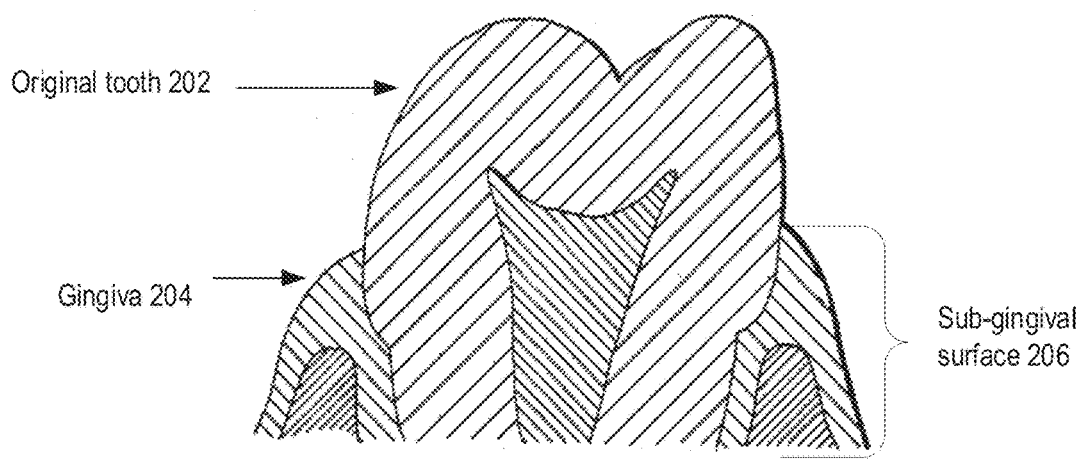
FIG. 2A illustrates original tooth prior to preparation of the tooth for a prosthodontic procedure, in accordance with some embodiments.
Figure 2B:
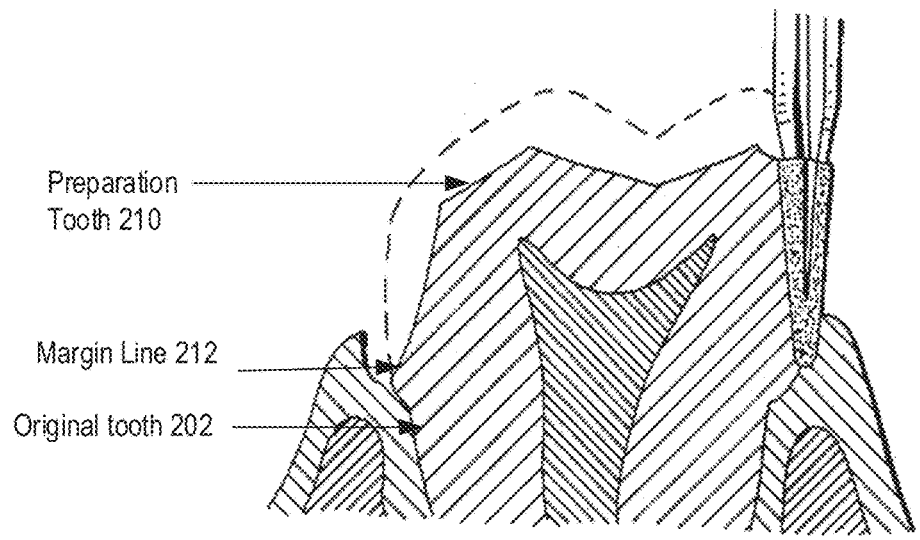
FIG. 2B illustrates the original tooth being prepared for a prosthodontic procedure, in accordance with some embodiments.
Figure 2C:
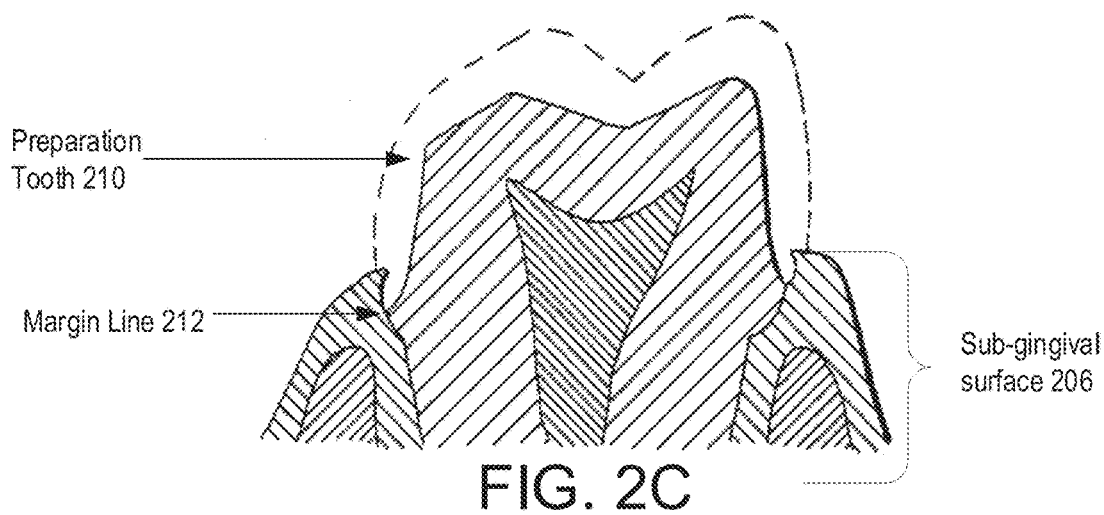
FIG. 2C illustrates the preparation tooth, in accordance with some embodiments.

FIGS. 2A-2C illustrate a creation of a preparation tooth, in accordance with some embodiments. FIG. 2A illustrates original tooth 202 (also referred to as "tooth 202" herein) prior to the preparation of the tooth 202 for a prosthodontic procedure, in accordance with some embodiments. Part of the tooth 202 extends away from the gingiva 204, and part of the tooth is surrounded by and/or underneath the gingiva 204. The surface of the part of the tooth 202 that is surrounded by and/or underneath the gingiva can be referred to as the sub-gingival surface 206 of the tooth (either the original tooth or the preparation tooth).

FIG. 2B illustrates the original tooth being prepared for a prosthodontic procedure, in accordance with some embodiments. As noted above, for many prosthodontic procedures (e.g., to create a crown, bridge, veneer, etc.), an original tooth 202 of a patient is ground down to a stump. The ground tooth is referred to herein as a preparation tooth 210 (also referred to as a "preparation 210" herein). The outline of the original tooth 202 is illustrated by dashed lines. The preparation tooth 210 has a margin line 212 which is a border between a natural (unground) portion of the preparation tooth and the prepared (ground) portion of the preparation tooth. As illustrated to the right-hand side, a dental tool is being used to grind down the original tooth 202. For purpose of clarity, after the original tooth has been ground down, the resulting tooth is referred to as a preparation tooth 210. The removed portion of the original tooth 202 is illustrated in FIG. 2B and FIG. 2C using a dashed line. In FIG. 2B and FIG. 2C the remaining portion of the original tooth 202 is shown below the margin line.

FIG. 2C illustrates the preparation tooth, in accordance with some embodiments. The preparation tooth 210 is typically created so that a crown or other dental prosthesis can be mounted or seated on the preparation tooth 210. In many instances, the margin line 212 of the preparation tooth is sub-gingival (below the gum line). The sub-gingival surface 206 of the preparation tooth 210 can include the portion of the preparation tooth 210 that is positioned below the gingiva. In the illustrated example, the sub-gingival surface 206 of the preparation tooth 210 includes some of the surface the ground portion of the preparation tooth (e.g., shoulder above the margin line 212), the margin line 212, and some of the surface of the original tooth 202.

Figure 3A:
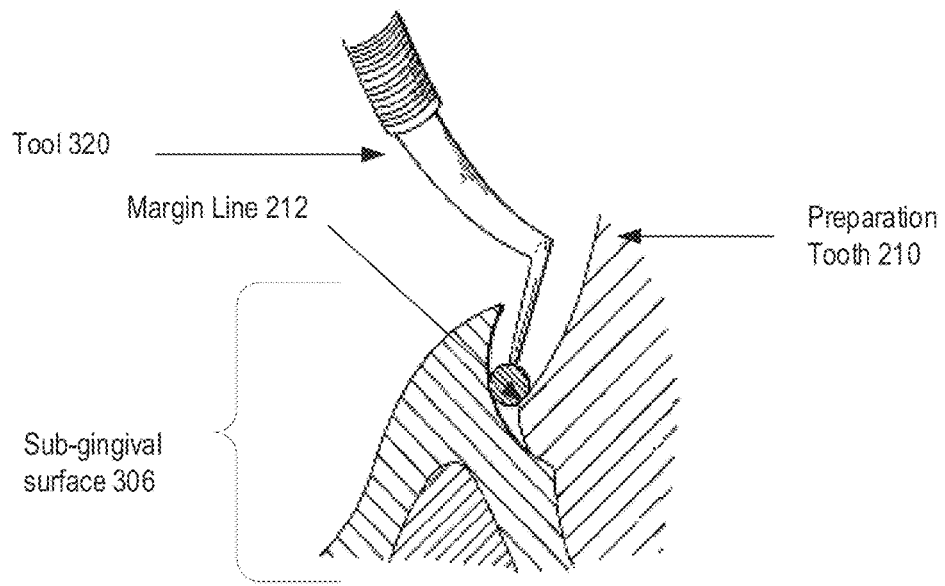
FIG. 3A illustrates the separation of the gingiva and sub-gingival surface of a tooth using a tool, in accordance with some embodiments.
Figure 3B:
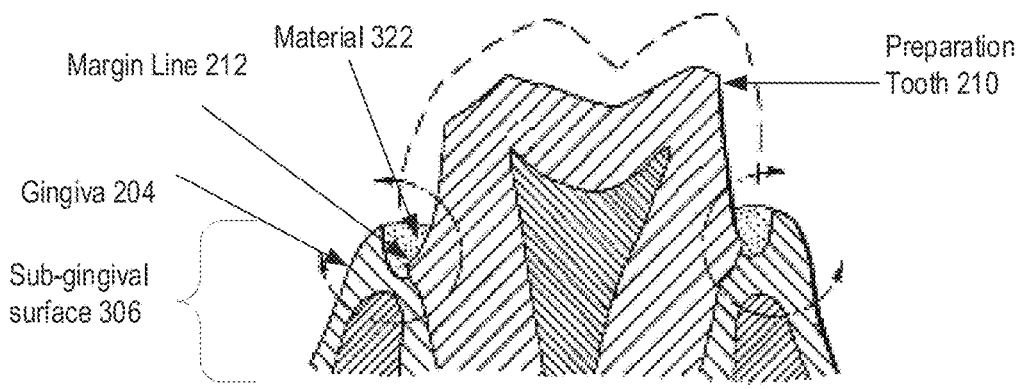
FIG. 3B illustrates a material disposed between a gingiva and the sub-gingival surface of the tooth, in accordance with some embodiments.
Figure 3C:
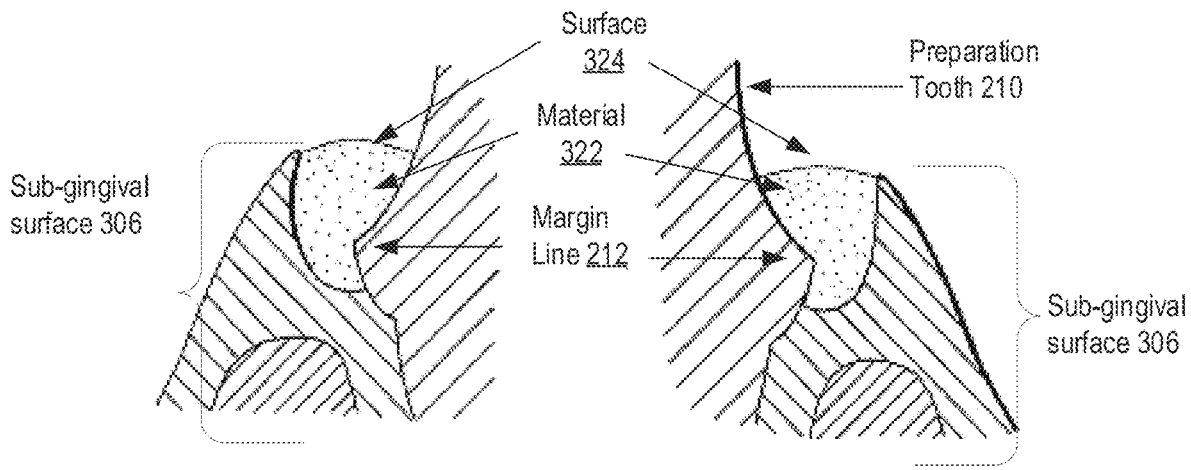
FIG. 3C illustrates an exploded view of a material disposed between a gingiva and the sub-gingival surface of the tooth, in accordance with some embodiments.

FIGS. 3A-3C illustrate an application of an at least partially transparent material between gingiva and the sub-gingival surface of a tooth, in accordance with some embodiments. FIG. 3A illustrates separation of the gingiva and sub-gingival surface of a tooth using a tool, in accordance with some embodiments. Elements of FIGS. 2A-2C are used herein to help describe the following figures. Tool 320 is an example of a dental tool that may be used to expose a portion of the margin line 212 and/or an area below the margin line 212 in the direction of the root of the preparation tooth 210. For example, tool 320 illustrates a retraction cord used to expose the sub-gingival surface 306 of preparation tooth 210, and in particular expose the sub-gingival surface 306 of the preparation tooth 210 below the margin line 212. Other types of tools that can be used to expose the sub-gingival surface 306 include dental probes, dental spatulas, triple syringes, and so on. It can be noted that the amount of sub-gingival surface 306 of the preparation tooth 210 below the margin line 212 that is exposed using techniques described herein can be less than conventional techniques, which can reduce the amount of damage done to a patient's gingiva.

While the sub-gingival surface 306 is exposed, an applicator such as a syringe is used to inject a material (e.g., an at least partially transparent material) into the area between the retracted gingiva and the preparation tooth. In one embodiment, the material is at least partially optically transparent for light having wavelengths of 600 through 700 nanometers (nm). FIG. 3B illustrates a material disposed between gingiva 204 and the sub-gingival surface 306 of the tooth, in accordance with some embodiments. Material 322 is disposed between the gingiva 204 and at least part of the sub-gingival surface 306 of the preparation tooth 210. In some embodiments, the material 322 is an at least partially transparent material. In particular, the material 322 is at least partially transparent to the optical signals (e.g., wavelengths of light) emitted by the probe of the intraoral scanner that is used to generate optical scan data of a tooth. The material 322 can allow the optical signals to traverse the material 322 from the external surface of the material 322 to the sub-gingival surface 306 of the preparation tooth 210 that is adjacent to the material 322. In some embodiments, the material 322 is a bio-compatible material that can be used inside a patient's mouth. In some embodiments, the material 322 is viscous and hardens with exposure to air. In some embodiments, the material 322 has a known refractive index (n). In some embodiments, the refractive index of the material 322 can be between 1 and 1.5. In some embodiments, the material 322 can be disposed between the gingiva 204 and the sub-gingival surface 306 of the preparation tooth using one or more dispensing tools. For example, material 322 can be disposed between the gingiva 204 and the sub-gingival surface 306 using a syringe.

In some embodiments, the material 322 separates that gingiva 204 and the sub-gingival surface 306 of the preparation tooth 210. The material 322 can hold the gingiva 204 apart from the sub-gingival surface 306 of the preparation tooth 210 so that a dental practitioner has enough time to perform an optical scanning of the preparation tooth 210, and in particular of the sub-gingival surface 306 of the preparation tooth 210.

It can be noted that the circular arrows on the right and the left of the preparation tooth 210 show areas that are further described with respect to FIG. 3C.

FIG. 3C illustrates an exploded view of a material disposed between a gingiva and the sub-gingival surface of the tooth, in accordance with some embodiments. Sub-gingival surface 306 of preparation tooth 210 is illustrated on the left-hand side and on the right-hand side of the figure. Above the margin line 212 is the surface of the preparation tooth 210 and below the margin line is the surface of the original tooth 202. The material 322 holds the gingiva away from the laterally adjacent sub-gingival surface 306 of the preparation tooth 210. The surface 324 of the material 322 is exposed between the gingiva 204 and the sub-gingival surface 306 of the preparation tooth 210.

Figure 4A:
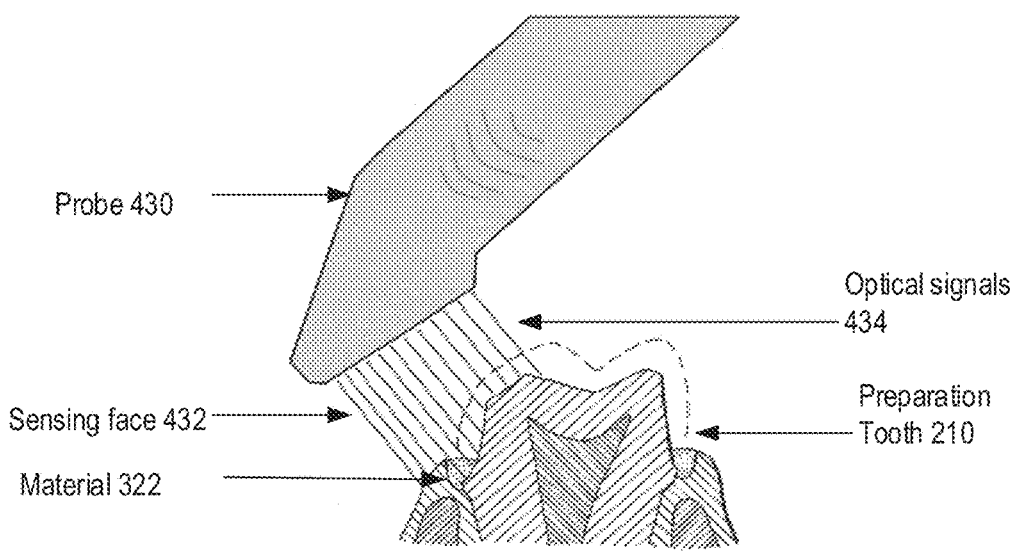
FIG. 4A illustrates a scanning of a tooth, in accordance with some embodiments.
Figure 4B:
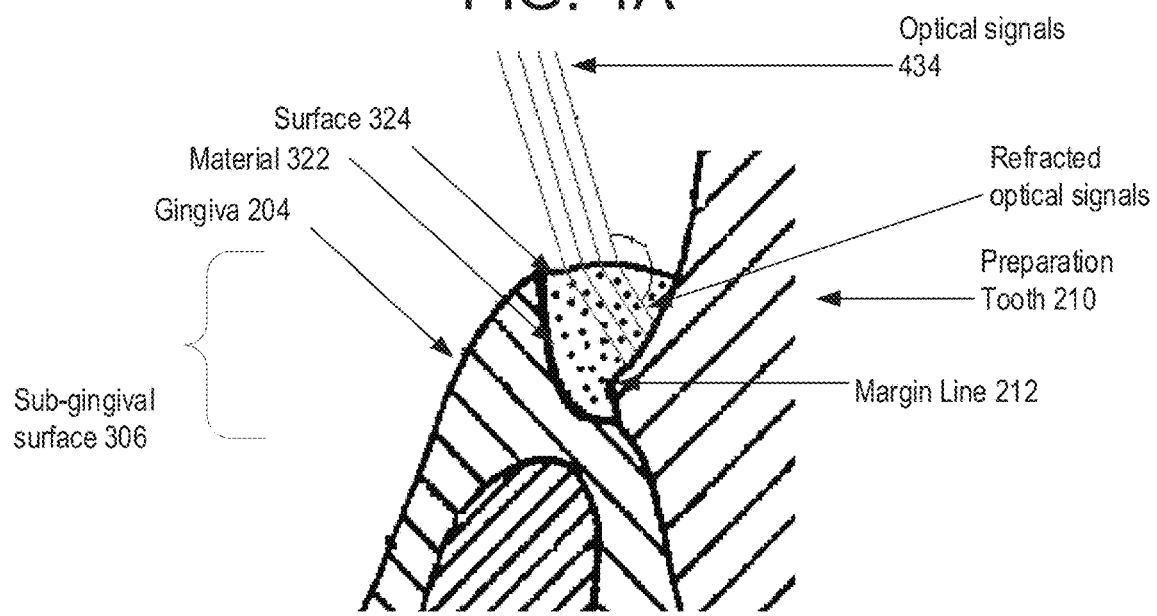
FIG. 4B is an exploded view of the preparation tooth during the scanning, in accordance with embodiments of the disclosure.
Figure 4C:
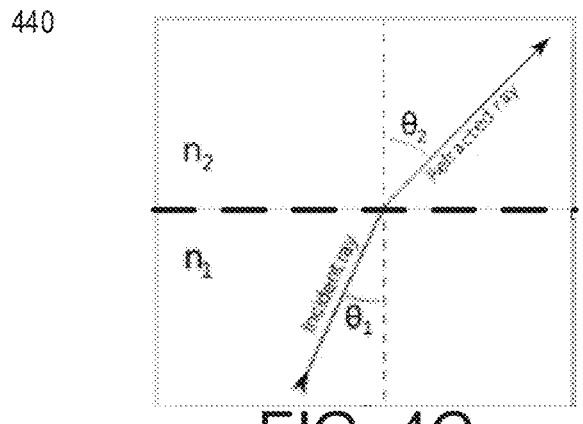
FIG. 4C includes a diagram that describes Snell's law application to aspects of the disclosure, in accordance with some embodiments.

FIGS. 4A-4B illustrate a scanning of a preparation tooth having an at least partially transparent material disposed between gingiva and the sub-gingival surface of a preparation tooth, in accordance with some embodiments. FIG. 4C includes a diagram that describes Snell's law application to aspects of the disclosure, in accordance with some embodiments. Elements of the preceding figures are used to help describe the following figures.

FIG. 4A illustrates a scanning of a preparation tooth, in accordance with some embodiments. In some embodiments, probe 430, such as an optical probe, can be a probe of an intraoral scanner, such as intraoral scanner 150 of FIG. 1. In some embodiments, probe 430 can include a sensing face 432 that emits and receives optical signals, such as optical signals 434. The optical signals 434 are incident on one or more surfaces and are reflected back to the sensing face 432 of the probe 430. The reflected optical signals are used to generate optical scan data. As illustrated, the optical signals are emitted from the probe 430 in the direction of the preparation tooth 210. As further illustrated, a portion of the optical signals 434 are directed to the material 322 that is disposed between the gingiva and the sub-gingival surface of the preparation tooth 210. A portion of the optical signals 434 are incident on the surface of the material 322 and traverse the material 322 to the sub-gingival surface of the preparation tooth 210.

FIG. 4B is an exploded view of the preparation tooth, in accordance with embodiments of the disclosure. FIG. 4C is used to help describe elements of FIG. 4B. Diagram 440 helps illustrate Snell's law application to embodiments of the present disclosure, In particular, diagram 440 is used to help describe the optical path of optical signals 434. Snell's law is a formula used to describe the relationship between the angles of incidence ($\theta_1$) and refraction ($\theta_2$), when referring to light or other waves passing through a boundary between two different isotropic media, such air and material 322.

Returning to FIG. 4B, the portion of optical signals 434 (hereinafter referred to as "optical signals 434") that are directed to the material 322 are illustrated. The optical signals 434 that are emitted by the probe 430 travel through a medium, such as air. The medium has a known refractive index ($n_1$), which is approximately 1 for air. The optical signals 434 are incident on the surface 324 of the material 322 at angles of incidence ($\theta_1$) (e.g., measured relative to normal the surface 324 the material 322). The material having a different refractive index ($n_2$) different than the medium causes the light to be refracted or bend. The refracted optical signals are refracted at angles of refraction ($\theta_2$) (e.g., measured relative to normal the surface 324 the material 322). The refracted optical signals traverse the material 322 and are incident upon the sub-gingival surface 306 of the preparation tooth 210. From the sub-gingival surface 306 of the preparation tooth 210, the refracted optical signals are reflected back to the sensing face 432 of the probe 430 based on a shape of the sub-gingival surface and an associated reflection angle off of the sub-gingival surface. The reflected light is then again refracted when it reaches the interface between the material and air. Thus, the pixel of a sensor that detects the refracted signal that was reflected off of the sub-gingival surface may be different from a pixel of the senor that would have received the signal if no material was present over the sub-gingival surface. For purposes of illustration, rather than limitation, the reflected optical signals are assumed to be retro-reflective optical signals that travel back to the sensing face 432 of the probe 430 on the same optical path from which the optical signals were emitted. It can be noted that reflected optical signals that travel back to the sensing face 432 of the probe 430 on a different optical path from which they are emitted is within the scope of the disclosure.

In some embodiments, the reflected optical signals carry information about the surfaces on which they were incident, such as the surface 324 of the material 322 and the sub-gingival surface 306 of the preparation tooth 210. In some embodiments, the reflected optical signals are used to generate an intraoral scan that includes first optical scan data of the sub-gingival surface 306 of the preparation tooth 210 and second optical scan data of the at least partially transparent material 322 (e.g., surface 324 thereof) overlying the sub-gingival surface 306 of the preparation tooth 210. For a given pixel of the sensor of the intraoral scanner, a first local peak in intensity may be detected that corresponds to surface 324 of the material, and a second local peak in intensity may be detected that corresponds to an underlying sub-gingival surface. Sub-gingival scanning module 118 and/or image processing module 118 may identify both local peaks and distinguish between the peaks representing the surface of the material and the peaks representing the sub-gingival surface. For example, the material may have a greater height (smaller distance from the probe) than sub-gingival surfaces. Accordingly, where two local maxima are detected for a single pixel, a local maxima with a greater height value (smaller distance value) may be determined to correspond to the material surface, and a local maxima with a smaller height value (greater distance value) may be determined to correspond to the sub-gingival surface. Thus, the height/depth of the material and the height/depth of the sub-gingival surface may both be determined.

In some embodiments, the first optical scan data of the sub-gingival surface 306 of the preparation tooth 210 does not accurately reflect the location of the sub-gingival surface 306 of the preparation tooth 210 at least because the optical signals traversing the material 322 have been refracted at angles of refraction ($\theta_2$), which may not be accounted for in the first optical scan data. Rather, the first optical scan data is calculated with the assumption that the trajectory of the optical signals that are incident upon the sub-gingival surface 306 of the preparation tooth 210 have not been refracted.

In some embodiments, to appropriately adjust the first optical scan data to reflect the actual coordinates of the sub-gingival surface 306 of the preparation tooth 210, coordinate offset data is determined. In some embodiments, the coordinate offset data is indicative of the sub-gingival surface 306 of the preparation tooth 210 on which the refracted optical signals that travelled through the at least partially transparent material 322 were incident. In some embodiments, to determine the coordinate offset data, the angles of refraction ($\theta_2$) of the refracted optical signals are determined. In one embodiment, a shape of the surface of the material is determined based on the determined heights/depths of the material. The shape of the material's surface and the known path of the light may be used to determine an angle of incidence of the light (e.g., light beams) with the material surface. This information along with the known refractive indexes of air and the material may then be used to determine the angles of refraction ($\theta_2$). The determined angles of refraction ($\theta_2$) of the refracted optical signals are used to determine the location of the sub-gingival surface 306 of the preparation tooth 210 on which the refracted optical signals were incident. Using the coordinate offset data, the sub-gingival surface 306 of the preparation tooth 210 can be determined by applying the coordinate offset data to the first optical scan data of the sub-gingival surface 306 of the preparation tooth 210. In some embodiments, the coordinates of the sub-gingival surface 306 of the preparation tooth 210 of the first optical scan data are adjusted using the coordinate offset data to account for the angles of refraction ($\theta_2$) of the refracted optical signals. In some embodiments, the determined sub-gingival surface 306 of the preparation tooth 210 can be used to generate a three-dimensional model of the preparation tooth 210. The 3D model of the preparation tooth 210 includes the sub-gingival surface 306 of the preparation tooth 210. In some embodiments, the 3D model of the preparation tooth 210 with the sub-gingival surface 306 of the preparation tooth 210 can include the sub-gingival surface 306 of the preparation tooth 210 including the margin line 212 and/or a surface above and/or below the margin line 212.

The following will describe the operation of determining the coordinate offset data for a single optical signal, e.g., a single optical beam, for purposes of illustration, rather than limitation. It can be noted that the following can be applied to any or many refracted optical signals. As noted above, the material 322 holds the gingiva 204 away from the sub-gingival surface 306 of the preparation tooth 210. The transparency of the material 322 allows an optical beam that is transmitted by the probe 430 to reach the sub-gingival surface 306 of the preparation tooth 210 and be reflected back to probe 430. According to Snell's law, if the angle of incidence ($\theta_1$) of the optical beam and the refractive index of the material 322 ($n_2$) are known, the angle of refraction ($\theta_2$) can be determined.

From the optical scan data, and in particular the second optical scan data, the distance between the probe 430 and the surface 324 of the material 322 (at the point on which the optical beam is incident) is known. From the optical scan data, and in particular the first optical scan data, the distance between the surface 324 of the material 322 (at the point on which the optical beam is incident) and the sub-gingival surface 306 of the preparation tooth 210 (at the point on which the optical beam is incident) is known. From the optical scan data and in particular the second optical scan data, a 3D model of the surface 324 of the material 322 is determined. As such, the X-, Y-, and Z-coordinates of the surface 324 of the material 322 at which the optical beam is incident are known from the 3D model. An angle of incidence ($\theta_1$) of the optical beam incident at a point at the surface 324 of the material 322 is determined (e.g., calculated) using the coordinates of the point at the surface 324 of the material at which the optical beam is incident. In some embodiments, the angle of incidence ($\theta_1$) can be calculated for the X- and Y-coordinates of the incident optical beam. The refractive index of the material 322 ($n_2$) is known, and the angle of refraction ($\theta_2$) can be determined (e.g., calculated) using the angle of incidence ($\theta_1$) and the coordinates of the point at the surface 324 of the material at which the optical beam is incident. In some embodiments, the angle of refraction ($\theta_2$) can be calculated for the X- and Y-coordinates of the refracted optical beam. Using the above information, the true X-coordinate and Y-coordinate of the point at the sub-gingival surface 306 of the preparation tooth 210 at which the refracted optical beam is incident beam are known (e.g., coordinate offset data). The true X-coordinate and Y-coordinate of the point at the sub-gingival surface 306 can be used to adjust the first optical scan data of the intraoral scan, and in particular adjust the first optical scan data associated with the particular optical beam. For example, an offset can be applied to the first optical scan data for the particular optical beam that reflects the difference between the true X-coordinate and Y-coordinate of the point at the sub-gingival surface 306 (associated with the coordinate offset data) and the X-coordinate and Y-coordinate of the point at the sub-gingival surface 306 associated with the first optical scan data. The first optical scan data can be modified using the coordinate offset data to generate modified first optical scan data. The modified first optical scan data can be used to determine a sub-gingival surface 306 of the preparation tooth 210, which can be further used to generate a 3D model of the preparation tooth 210 that includes the sub-gingival surface 306 of the preparation tooth 210.

The methods 500 and 552 may be performed by processing logic that may comprise hardware (e.g., circuitry, dedicated logic, programmable logic, microcode, etc.), software (e.g., instructions run on a processing device to perform hardware simulation), or a combination thereof. In some embodiments, at least some operations of the method 500 and 552 are performed by sub-gingival scanning module 118 of FIG. 1. In some embodiments, at least some operations of the method and 552 are performed by a computing device executing dental modeling logic, such as dental modeling logic 650 of FIG. 6. The dental modeling logic 650 may be, for example, a component of an intraoral scanning apparatus that includes a handheld intraoral scanner and a computing device operatively coupled (e.g., via a wired or wireless connection) to the handheld intraoral scanner. Alternatively, or additionally, the dental modeling logic may execute on a computing device at a dental lab.

For simplicity of explanation, the methods 500 and 552 are depicted and described as a series of acts. However, acts in accordance with this disclosure can occur in various orders and/or concurrently, and with other acts not presented and described herein. Furthermore, not all illustrated acts may be required to implement the methods 550 or 552 in accordance with the disclosed subject matter. In addition, those skilled in the art will understand and appreciate that the method could alternatively be represented as a series of interrelated states via a state diagram or events.

Figure 5A:
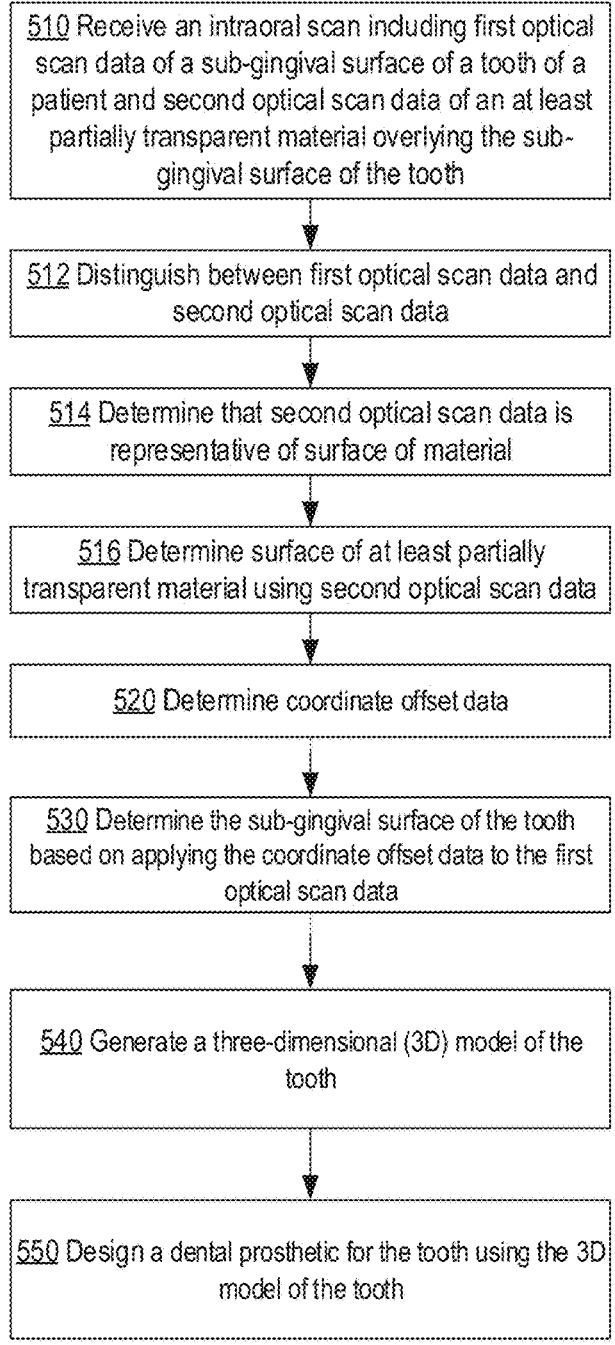
FIG. 5A illustrates a method related to intraoral scanning and generation of virtual 3D models of dental sites, in accordance with some embodiments of the disclosure.

FIG. 5A illustrates a method related to intraoral scanning and generation of virtual 3D models of dental sites, in accordance with some embodiments of the disclosure.

At block 510 of method 500, processing logic receives an intraoral scan including first optical scan data of a sub-gingival surface of a tooth of a patient and second optical scan data of an at least partially transparent material overlying the sub-gingival surface of the tooth. The at least partially transparent material is disposed between a gingiva of the patient and the sub-gingival surface of the tooth and separates the gingiva from the sub-gingival surface of the tooth.

At block 512, processing logic distinguishes (e.g., differentiates) between the first optical scan data and the second optical scan data. As noted above, the optical signals (e.g., light) are incident both the surface of the material and the sub-gingival surface of the preparation tooth. As the surface on which the incident light hits is an uneven surface, illuminated points are displaced from one another along the Z axis, at different ($X_i$, $Y_i$) locations. Thus, while a point at one location may be in focus of the confocal focusing optics, points at other locations may be out-of-focus, Therefore, the light intensity of returned light of the focused points will be at its peak, while the light intensity at other points will be off peak. Thus, for each illuminated point or area, multiple measurements of light intensity are made at different positions along the Z-axis. For each of such ($X_i$, $Y_i$) location, the derivative of the intensity over distance (Z) may be made, with the $Z_i$ yielding maximum derivative, $Z_0$, being the in-focus distance. In some embodiments, the measured intensity of light reflected from the surface of the material is greater than the measured intensity of light reflected from the sub-gingival surface of the tooth. In some embodiments, the measured intensity of light reflected from the surface is has the maximum intensity and the measured intensity of light reflected from the sub-gingival surface of the tooth has the second maximum intensity. The measured intensity of light having the maximum intensity can be associated with the second optical scan data corresponding to the surface of the material, and measured intensity of the light having the second maximum intensity can be associated with the first optical scan data corresponding to the sub-gingival surface of the preparation tooth. Thus, the first optical scan data is distinguished from the second optical scan data.

In some embodiments, two different intensity peaks may be associated with the same pixel, where one of the peaks represents a surface of the material and another peak represents the sub-gingival surface. For a given pixel of the sensor of the intraoral scanner, a first local peak in intensity may be detected that corresponds to surface of the material, and a second local peak in intensity may be detected that corresponds to an underlying sub-gingival surface. Sub-gingival scanning module and/or image processing module 118 may identify both local peaks and distinguish between the peaks representing the surface of the material and the peaks representing the sub-gingival surface. For example, the material may have a greater height (smaller distance from the probe) than sub-gingival surfaces. Accordingly, where two local maxima are detected for a single pixel, a local maxima with a greater height value (smaller distance value) may be determined to correspond to the material surface, and a local maxima with a smaller height value (greater distance value) may be determined to correspond to the sub-gingival surface. Thus, the height/depth of the material (e.g., second optical scan data) and the height/depth of the sub-gingival surface (e.g., first optical scan data) may both be determined, which distinguishes the first optical scan data form the second optical scan data. In other embodiments, a combination of the embodiments that use light intensity and height values to distinguish (e.g., differentiate) the first optical scan data form the second optical scan data can be implemented.

At block 514, processing logic determines that second optical scan data is representative of the surface of the material. As noted above, once the first optical scan data is distinguished form the second optical scan data, the second optical scan data is determined to represent the surface of the material. For example, optical scan data having on the second maximum intensity or greater distance value can be determined as the second optical scan data.

At block 516, processing logic determines that the surface of the at least partially transparent material using the second optical scan data. In some embodiments, the second optical scan data is transformed into a 3D surface (e.g., X-, Y-, and Z-coordinates) of the at least partially transparent material.

At operation 520, processing logic determines coordinate offset data. The coordinate offset data is indicative of locations on the sub-gingival surface of the tooth on which refracted optical signals that travelled through the at least partially transparent material were incident. In some embodiments, to differentiate the first optical scan data from the second optical scan data processing logic determines coordinate offset data. In some embodiments, to determine the coordinate offset data, processing logic determines angles of refraction of the refracted optical signals to further determine the locations of the sub-gingival surface of the tooth on which the refracted optical signals were incident. In some embodiments, determining the angles of refraction is based on a predetermined refractive index of the at least partially transparent material.

In some embodiments, to determine the coordinate offset data, processing logic determines a 3D model of a surface of the at least partially transparent material that is exposed between the gingiva and the sub-gingival surface of the tooth based on the second optical scan data of the at least partially transparent material overlying the sub-gingival surface of the tooth. Processing logic further determines angles of incidence of incident optical signals that are incident on the surface of the at least partially transparent material. The angles of refraction can be determine using the angles of incidence of the optical signals and the refractive index of the material.

At operation 530, processing logic determines the sub-gingival surface of the tooth. The determination is based on applying the coordinate offset data to the first optical scan data. In some embodiments, the determined sub-gingival surface of the tooth of the 3D model includes a surface of the tooth below the margin line of the tooth. In some embodiments, to determine the sub-gingival surface of the tooth based on applying the coordinate offset data to the first optical scan data, processing logic adjusts coordinates of the sub-gingival surface of the tooth of the first optical scan data using the coordinate offset data to account for the angles of refraction of the refracted optical signals.

At operation 540, processing logic generates a three-dimensional (3D) model of the tooth. The generation of the 3D model of the tooth is based on at least in part on the intraoral scan. The 3D model of the tooth includes the determined sub-gingival surface of the tooth.

At operation 550, processing logic designs a dental prosthetic for the tooth using the 3D model of the tooth. The 3D model of the tooth includes the determined sub-gingival surface of the tooth.

Figure 5B:
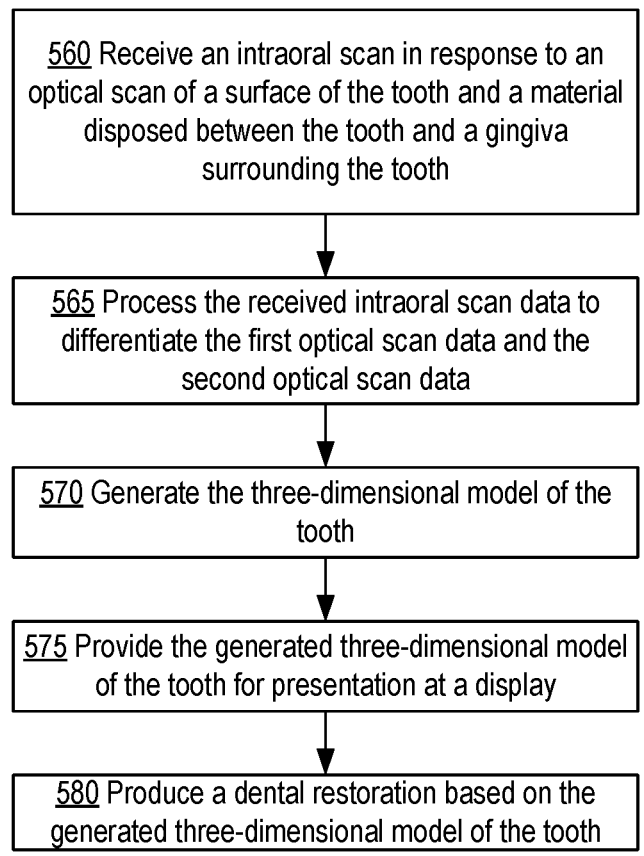
FIG. 5B illustrates another method related to intraoral scanning and generation of virtual 3D models of dental sites, in accordance with some embodiments of the disclosure.

FIG. 5B illustrates another method related to intraoral scanning and generation of virtual 3D models of dental sites, in accordance with some embodiments of the disclosure.

At operation 560, processing logic receives an intraoral scan in response to an optical scan of a surface of the tooth and a material disposed between the tooth and a gingiva surrounding the tooth. In some embodiments, processing logic receives intraoral scan data including first optical scan data, second optical scan data and third optical scan data in response to an optical scan of a surface of the tooth and a material disposed between the tooth and a gingiva surrounding the tooth. The material separates the surrounding gingiva from the tooth and covering a sub-gingival surface of the tooth. In some embodiments, wherein the material is at least partially optically transparent to the optical scan. In some embodiments, the first, second and third optical scan data can be collected from a single optical scan of the dental side (e.g., collected during a single intraoral scanning rather than having multiple optical scans to generate each of the first, second, and third optical scan data).

At operation 565, processing logic processes the received intraoral scan data to differentiate the first optical scan data and the second optical scan data. In some embodiments, processing logic processes the received intraoral scan data to differentiate the first optical scan data associated with the sub-gingival surface of the tooth and the second optical scan data associated with the material covering the sub-gingival surface of the tooth.

In some embodiments, to processes the received intraoral scan data to differentiate first optical scan data and second optical scan data processing logic determines coordinate offset data indicative of locations on the sub-gingival surface of the tooth on which refracted optical signals that travelled through the material were incident.

In some embodiments, to determining the coordinate offset data, processing logic determines angles of refraction of the refracted optical signals to determine the locations of the sub-gingival surface of the tooth on which the refracted optical signals were incident. In some embodiments, processing logic adjusts coordinates of the sub-gingival surface of the tooth of the first optical scan data using the coordinate offset data to account for the angles of refraction of the refracted optical signals.

In some embodiments, to determining the coordinate offset data processing logic determines a 3D model of a surface of the material that is disposed between the tooth and the gingiva surrounding the tooth based on the second optical scan data associated with the material covering the sub-gingival surface of the tooth. Processing logic determines angles of incidence of incident optical signals that are incident on the surface of the material.

At operation 570, processing logic generates the three-dimensional model of the tooth. In some embodiments, generating the three-dimensional model of the tooth is based on the first optical scan data that is associated with the sub-gingival surface of the tooth and the third optical scan data associated with the tooth surface that is not covered by the material such that the three-dimensional model of the tooth includes the sub-gingival surface of the tooth.

At operation 575, processing logic provides the generated three-dimensional model of the tooth for presentation at a display.

At operation 580, processing logic produces a dental restoration (e.g., dental prosthetic) based on the generated three-dimensional model of the tooth.

Figure 6:
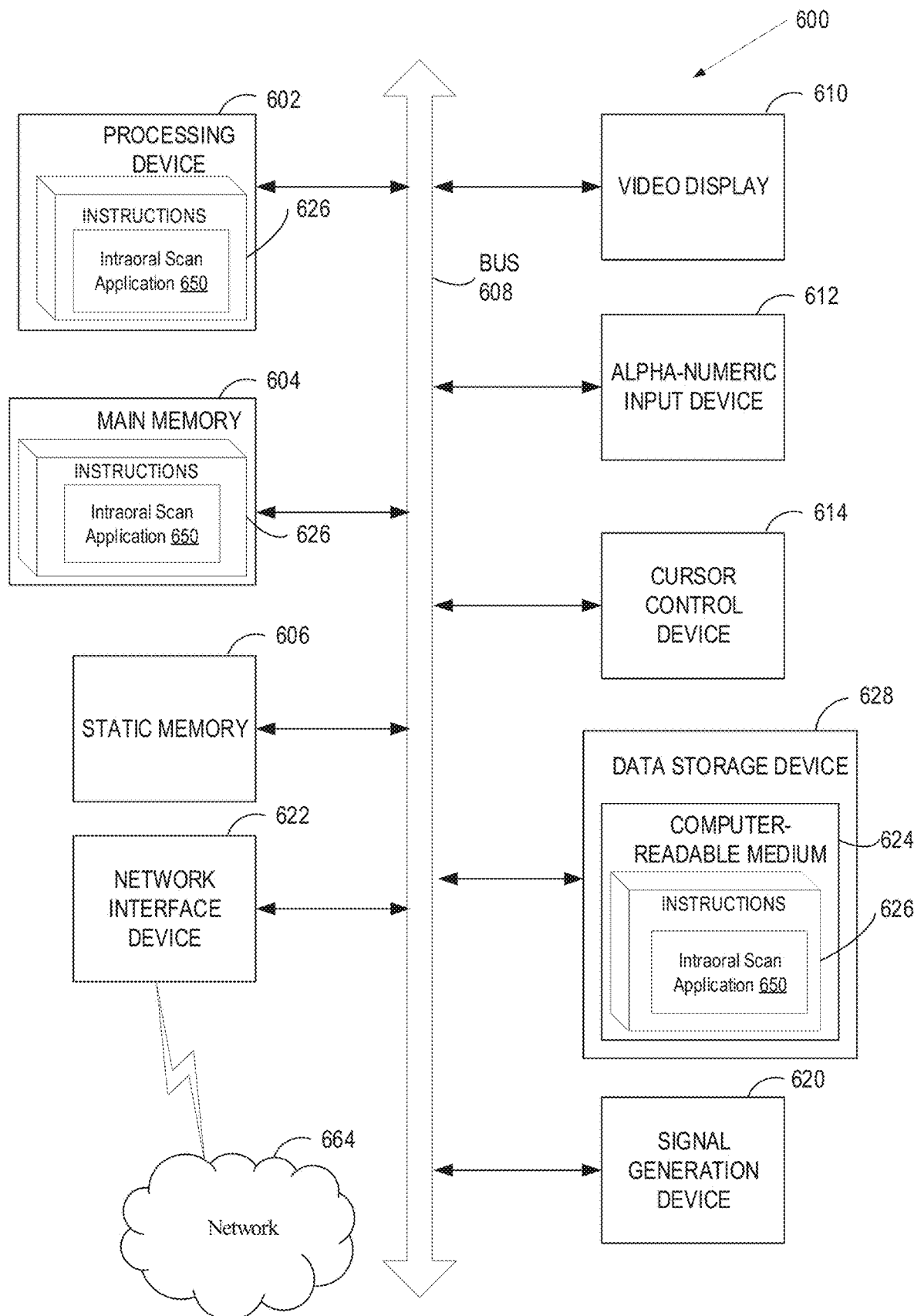
FIG. 6 illustrates a block diagram of an example computing device, in accordance with embodiments of the present disclosure.

FIG. 6 illustrates a diagrammatic representation of a machine in the example form of a computing device 600 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The computing device 600 may correspond, for example, to computing device 105 and/or computing device 106 of FIG. 1. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 600 includes a processing device 602, a main memory 604 (e.g., read-only memory (ROM), flash memory, dynamic random access memory (DRAM) such as synchronous DRAM (SDRAM), etc.), a static memory 606 (e.g., flash memory, static random access memory (SRAM), etc.), and a secondary memory (e.g., a data storage device 628), which communicate with each other via a bus 608.

Processing device 602 represents one or more general-purpose processors such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. Processing device 602 is configured to execute the processing logic (instructions 626) for performing operations and steps discussed herein.

The computing device 600 may further include a network interface device 622 for communicating with a network 664. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse), and a signal generation device 620 (e.g., a speaker).

The data storage device 628 may include a machine-readable storage medium (or more specifically a non-transitory computer-readable storage medium) 624 on which is stored one or more sets of instructions 626 embodying any one or more of the methodologies or functions described herein, such as instructions for dental modeling logic 650. A non-transitory storage medium refers to a storage medium other than a carrier wave. The instructions 626 may also reside, completely or at least partially, within the main memory 604 and/or within the processing device 602 during execution thereof by the computer device 600, the main memory 604 and the processing device 602 also constituting computer-readable storage media.

The computer-readable storage medium 624 may also be used to intraoral scan application 650, which may correspond to similarly named intraoral scan application 115 of FIG. 1A and/or intraoral scan application 29 of FIG. 1C, and which may perform the operations described herein above. The computer readable storage medium 624 may also store a software library containing methods for the intraoral scan application 650. While the computer-readable storage medium 624 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method for generating a three-dimensional model of a tooth, wherein the three-dimensional model of the tooth includes a sub-gingival surface of the tooth, the method comprising:

receiving intraoral scan data comprising first optical scan data, second optical scan data and third optical scan data in response to an optical scan of a surface of the tooth and a material disposed between the tooth and a gingiva surrounding the tooth, the material separating the surrounding gingiva from the tooth and covering a sub-gingival surface of the tooth;

processing the received intraoral scan data to differentiate the first optical scan data associated with the sub-gingival surface of the tooth and the second optical scan data associated with the material covering the sub-gingival surface of the tooth; and generating the three-dimensional model of the tooth based on the first optical scan data that is associated with the sub-gingival surface of the tooth and the third optical scan data associated with the tooth surface that is not covered by the material such that the three-dimensional model of the tooth includes the sub-gingival surface of the tooth.

2. The method of claim 1, wherein the material is at least partially optically transparent to the optical scan.

3. The method of claim 1, further comprising providing the generated three-dimensional model of the tooth for presentation at a display.

4. The method of claim 1, further comprising producing a dental restoration based on the generated three-dimensional model of the tooth.

5. The method of claim 1, wherein processing the received intraoral scan data to differentiate the first optical scan data and the second optical scan data comprises determining coordinate offset data indicative of locations on the sub-gingival surface of the tooth on which refracted optical signals that travelled through the material were incident.

6. The method of claim 5, wherein determining the coordinate offset data comprises:

determining angles of refraction of the refracted optical signals to determine the locations of the sub-gingival surface of the tooth on which the refracted optical signals were incident; and adjusting coordinates of the sub-gingival surface of the tooth of the first optical scan data using the coordinate offset data to account for the angles of refraction of the refracted optical signals.

7. The method of claim 6, wherein determining the coordinate offset data comprises:

determining a three-dimensional model of a surface of the material that is disposed between the tooth and the gingiva surrounding the tooth based on the second optical scan data associated with the material covering the sub-gingival surface of the tooth; and determining angles of incidence of incident optical signals that are incident on the surface of the material.

8. A system comprising:

an optical probe with a sensing face, the optical probe to emit optical signals and receive reflected optical signals; and an optical imaging device, coupled to the optical probe, to:

receive intraoral scan data comprising first optical scan data, second optical scan data and third optical scan data in response to an optical scan of a surface of a tooth and a material disposed between the tooth and a gingiva surrounding the tooth, the material separating the surrounding gingiva from the tooth and covering a sub-gingival surface of the tooth;

process the received intraoral scan data to differentiate the first optical scan data associated with the sub-gingival surface of the tooth and the second optical scan data associated with the material covering the sub-gingival surface of the tooth; and generate a three-dimensional model of the tooth based on the first optical scan data that is associated with the sub-gingival surface of the tooth and the third optical scan data associated with the tooth surface that is not covered by the material such that the three-dimensional model of the tooth includes the sub-gingival surface of the tooth.

9. The system of claim 8, wherein the material is at least partially optically transparent to the optical scan.

10. The system of claim 8, the optical imaging device further to:

provide the generated three-dimensional model of the tooth for presentation at a display.

11. The system of claim 8, wherein the optical imaging device further to:

produce a dental restoration based on the generated three-dimensional model of the tooth.

12. The system of claim 8, wherein to process the received intraoral scan data to differentiate the first optical scan data and the second optical scan data the optical imaging device further to:

determine coordinate offset data indicative of locations on the sub-gingival surface of the tooth on which refracted optical signals that travelled through the material were incident.

13. The system of claim 12, wherein to determine the coordinate offset data the optical imaging device to:

determine angles of refraction of the refracted optical signals to determine the locations of the sub-gingival surface of the tooth on which the refracted optical signals were incident; and adjust coordinates of the sub-gingival surface of the tooth of the first optical scan data using the coordinate offset data to account for the angles of refraction of the refracted optical signals.

14. The system of claim 13, wherein to determine the coordinate offset data the optical imaging device to:

determine a three-dimensional model of a surface of the material that is disposed between the tooth and the gingiva surrounding the tooth based on the second optical scan data associated with the material covering the sub-gingival surface of the tooth; and determine angles of incidence of incident optical signals that are incident on the surface of the material.

15. A non-transitory computer-readable medium comprising instructions that, responsive to execution by a processing device, cause the processing device to perform operations comprising:

receiving intraoral scan data comprising first optical scan data, second optical scan data and third optical scan data in response to an optical scan of a surface of a tooth and a material disposed between the tooth and a gingiva surrounding the tooth, the material separating the surrounding gingiva from the tooth and covering a sub-gingival surface of the tooth;

processing the received intraoral scan data to differentiate the first optical scan data associated with the sub-gingival surface of the tooth and the second optical scan data associated with the material covering the sub-gingival surface of the tooth; and generating a three-dimensional model of the tooth based on the first optical scan data that is associated with the sub-gingival surface of the tooth and the third optical scan data associated with the tooth surface that is not covered by the material such that the three-dimensional model of the tooth includes the sub-gingival surface of the tooth.

16. The non-transitory computer-readable medium of claim 15, wherein the material is at least partially optically transparent to the optical scan.

17. The non-transitory computer-readable medium of claim 15, the operations further comprising:

providing the generated three-dimensional model of the tooth for presentation at a display.

18. The non-transitory computer-readable medium of claim 15, the operations further comprising:

producing a dental restoration based on the generated three-dimensional model of the tooth.

19. The non-transitory computer-readable medium of claim 15, wherein processing the received intraoral scan data to differentiate the first optical scan data and the second optical scan data comprises determining coordinate offset data indicative of locations on the sub-gingival surface of the tooth on which refracted optical signals that travelled through the material were incident.

20. The non-transitory computer-readable medium of claim 19, wherein determining the coordinate offset data comprises:

determining angles of refraction of the refracted optical signals to determine the locations of the sub-gingival surface of the tooth on which the refracted optical signals were incident;

adjusting coordinates of the sub-gingival surface of the tooth of the first optical scan data using the coordinate offset data to account for the angles of refraction of the refracted optical signals;

determining a three-dimensional model of a surface of the material that is disposed between the tooth and the gingiva surrounding the tooth based on the second optical scan data associated with the material covering the sub-gingival surface of the tooth; and determining angles of incidence of incident optical signals that are incident on the surface of the material.

* * * * *